United States Patent [19]

Waybright et al.

[11] Patent Number: 5,549,671
[45] Date of Patent: Aug. 27, 1996

[54] ADJUNCTIVE FILLER MATERIAL FOR FLUID-FILLED PROSTHESIS

[75] Inventors: Richard S. Waybright, Lompoc; Daniel A. Carlisle, Santa Barbara, both of Calif.

[73] Assignee: McGhan Medical Corporation, Santa Barbara, Calif.

[21] Appl. No.: 365,202

[22] Filed: Dec. 28, 1994

[51] Int. Cl.$^6$ .............................. A61F 2/12; A61F 2/52; A61F 2/02
[52] U.S. Cl. ...................... 623/8; 623/7; 623/11
[58] Field of Search ............................. 623/8, 7, 11, 17, 623/66

[56] References Cited

U.S. PATENT DOCUMENTS

| | | | |
|---|---|---|---|
| 3,986,213 | 10/1976 | Lynch | 623/8 |
| 4,955,907 | 9/1990 | Ledergerber | 623/8 |
| 5,246,454 | 9/1993 | Peterson | 623/8 |

*Primary Examiner*—Debra S. Brittingham
*Attorney, Agent, or Firm*—Michael G. Petit

[57] ABSTRACT

A fluid-filled mammary prosthesis for implantation beneath the skin of a patient comprising a shell and an adjunctive filler. The shell is preferably a closed silicone elastomer envelope having an interior volume and valve for filling. The filler material is a mixture of a fluid such as saline and an adjunct consisting of a plurality of hollow silicone beads having two or more fenestrations within the wall of each bead which provide fluid communication between the outside of the bead and the hollow interior. The beads are packed into the shell prior to the introduction of fluid into the interior of the shell. The beads serve as a baffle to prevent unwanted hydraulic behavior of the fluid portion of the filler material and also serve to help maintain the anatomical profile of the implant. The hollow beads, which range in size from about 7/32 inch to ½ inch in inside diameter, may be conveniently made by injection molding. The adjunctive filler may be a plurality of beads of a particular size or a mixture of different sized beads.

10 Claims, 1 Drawing Sheet

ADJUNCTIVE FILLER MATERIAL FOR FLUID-FILLED PROSTHESIS

BACKGROUND OF THE INVENTION

1. Field of the Invention

This invention relates generally to a filler for a prosthesis for augmentation and reconstruction of a portion of the body and more particularly to an adjunctive filler material for a fluid-fill breast prosthesis.

2. Prior Art

There have been many attempts to improve the hydraulic and/or anatomical behavior of fluid-filled breast prostheses. With prior art implantable fluid-filled prostheses, particularly saline filled prostheses, a number of problems arise. The prosthesis, which is filled with a fluid having different properties than tissue, must preferably preserve the natural softness and resiliency of the body tissue that is being replaced. The most common type of prosthesis used for this purpose has traditionally consisted of a hollow container or shell made of silicone or polyurethane which is molded to the desired anatomical size and shape. The shell is then filled with a material which can be cured to a gel-like consistency such as silicone gel.

Silicone gels have work well in the past to provide a prosthesis having a shape and hydraulic properties similar to that of normal tissue. Saline filled implants, however, do not have sufficient rigidity to retain a particular shape when the patient hosting the implant changes position. The outer shell of the prosthesis is flexible which permits a change in the shape of the prosthesis under the shifting weight of the saline inside the prosthesis.

Saline, having a density of about 1 gram per ml is denser than breast tissue having a density of around 0.8 grams per ml. A saline-filled prosthesis may produce wrinkles in the upper portion and tends to bulge excessively at the lower portion when the wearer stands or leans forward even though the prosthesis is properly shaped when implanted (i.e., when the patient is lying down). Moreover, when the patient is in motion, the hydraulic difference between saline and breast tissue produces a sloshing or gurgling sound within the prosthesis which is esthetically unpleasing.

To overcome these and other problems, various solutions have been attempted. Particular reference is made to U.S. Pat. No. 4,650,487 to Chaglassian, U.S. Pat. No. 4,790,848 to Cronin and, most particularly, to U.S. Pat. No. 5,171,269 to Bark. Bark teaches the use of a baffling material comprising a fibrous insoluble material which prevents the saline in a saline filled implant from sloshing. Other such fillers include various baffling systems and/or compositions such as cellulose, hemicellulose chitosan and the like. To date, none of the non-silicone gel type fillers provide an esthetically pleasing match between normal breast tissue and the filler material.

SUMMARY OF THE INVENTION

It is an object of this invention to provide a filler material for prosthesis.

It is another object of this invention to provide biocompatible adjunctive filler which may be used in combination with saline or another fluid to fill a implantable prosthesis.

It is another object of this invention to provide a filler material for a breast implant which helps retain the anatomical profile of the implant during changes in position.

It is still another object of this invention to provide an adjunctive filler material for a fluid filled implant which, when used in combination with a suitable fluid to fill an implantable prosthesis, has hydraulic properties which are more similar to that of the tissue than the implant filled with fluid alone.

The features of the invention believed to be novel are set forth with particularity in the appended claims. However, the invention itself both as to organization and method of operation together with further objects and advantages therefor may best be understood by reference to the following description taken in conjunction with the accompanying drawings in which:

DESCRIPTION OF THE PREFERRED EMBODIMENTS

Figure 1:
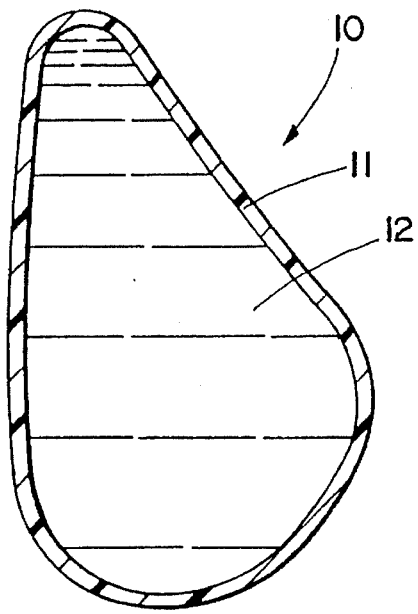
FIG. 1 is a cross-sectional view of a prior art fluid-filled breast prosthesis.

It is convenient to make reference to a particularly exemplary embodiment of the invention in order to teach the features and advantages of the invention in context of actual use. A fluid filled breast implant is such an embodiment of the present invention. The discussion to follow, while directed to a breast implant is intended to extend to other fluid-filled prostheses. A fluid-filled breast prosthesis 10 in accordance with the prior art is shown in FIG. 1. The breast prosthesis 10 comprises an elastomer outer shell 11 and a fluid filler material 12.

Figure 2:
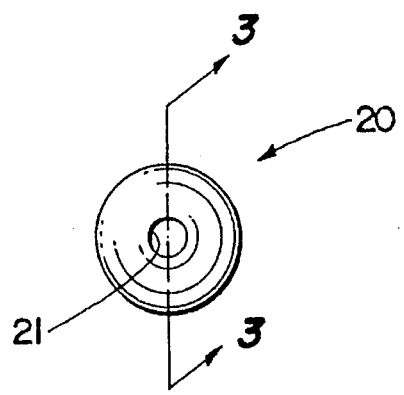
FIG. 2 is a perspective view of an adjunctive filler consisting of a hollow silicone inner bead in accordance with the present invention.
Figure 3:
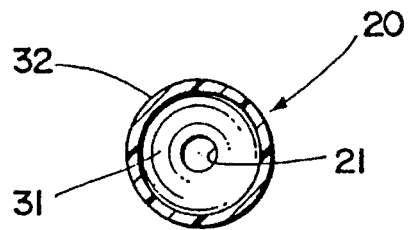
FIG. 3 is a cross-sectional view of the inner bead of FIG. 2 taken along section line 3—3.
Figure 5:
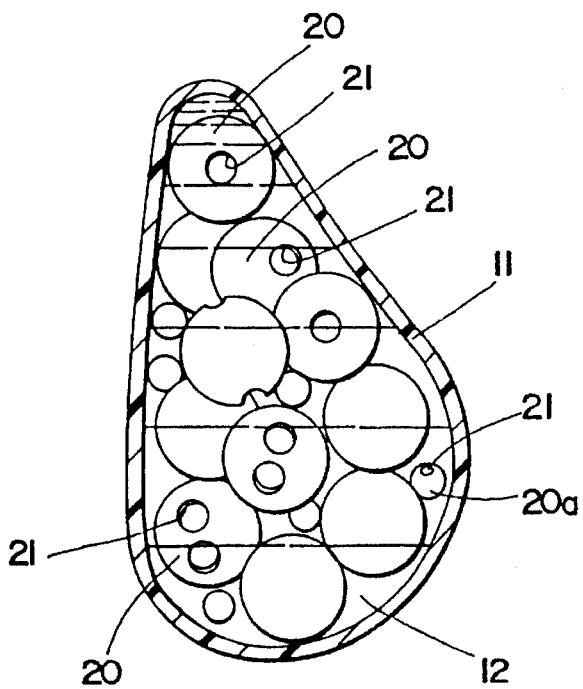
FIG. 5 is a cross-sectional view of a saline-filled breast prosthesis filled in combination with the inner beads of the present invention.

Turning now to FIG. 2, an inner shell comprising small hollow spherical bead generally designated at the numeral 20 is shown in perspective. The inner shell 20, referred to herein alternatively as the inner shell or inner bead, or simply, the bead, has a hollow interior 31 (FIG. 3) which is in fluid communication with the exterior of the inner shell 20 by means of at least two holes or fenestrations 21. The inner shells 20 are provided with at least two fenestrations 21 to enable the fluid from within an implant in which the inner shells 20 are dispersed, to enter the interior 31 of the inner shell displacing any air trapped therewithin. The removal of air from the interior of the inner shell is greatly facilitated by providing more than one hole 21 in the wall of the inner shell 20. By varying the size of the hole 21 with respect to the diameter of the inner shell 20, the rigidity of the inner shell 20 may be varied. The rigidity of the inner shell 20 can also be varied, of course, by varying the wall thickness of the inner shell or the durometer of the silicone used to mold the inner shell.

The inner shell 20 is easily made by dipping a rod having a ball or sphere axially mounted on the shaft thereof into a dispersion of silicone and curing the layer deposited thereon. Repetitive dips result in a casting which can be peeled from the ball leaving two holes where the rod enters and exits the ball. The inner shells 20 have been made in a variety of inner diameters ranging in size from 7/32 inch to 1/2 inch. The wall 32 thickness of the inner shell 20 for the smallest diameter inner shells range from 0.020 inches to 0.022 inches. The diameter of the dipping rod, which is the same as the diameter of the holes 21, is 1/16 inch. For the smallest inner shells, that is, the 7/32 inch inner diameter shells, approximately 900 shells are required to fill a style 168 breast implant (McGhan Medical Company, Santa Barbara, Calif.). This style breast implant corresponds to an interior volume of approximately 150 cc contained within the outer shell.

Figure 4:
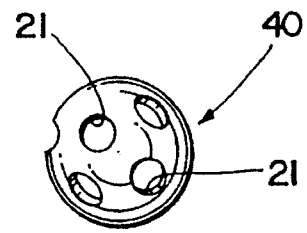
FIG. 4 is a perspective view of yet another embodiment of an adjunctive filler inner bead having multiple holes in the wall thereof in accordance with the present invention.

While the above mentioned method of making inner shells is suitable for making small quantities of these adjunctive fillers for the purpose of testing, it is not the preferred method for making the large quantity of inner shells required for production. For production it is preferable to injection mold the inner shells. The inner shells 20 may be packed into an outer shell 11 of an implantable prosthesis through a hole. The beads need not be the same size but may be a plurality of sizes. In addition, the beads may have more than two openings in the wall thereof. This is shown in FIG. 4 where a bead 40 is presented which has more than two holes 21 connecting the inner volume (not shown) with the exterior of the bead. In general, the more holes that are placed in the surface of the shell, the more flexible or supple the inner shell will be. This provides design flexibility for improving the feel of the implant when the implant is packed with inner beads and filled with saline. Alternatively, the wall 32 of the bead may be made thicker or thinner as desired to provide the necessary resilience.

In practice, the shell 11 is preferably prepared by dipping a mold or mandrel which has the anatomical shape desired for the prosthesis into a dispersion of elastomer. The mandrel is usually a solid object having the desired shape of the prosthesis and attached to a dipping rod which is used to hold the mandrel during dipping and curing. After the mandrel is dipped in the dispersion of elastomer, the mandrel is removed and the coating partially cured. Repetitive dipping followed by vulcanization provides a shell having the desired prosthetic shape. The shell is peeled from the mandrel by means of a hole cut in the shell around the dipping rod to provide a container having the approximate shape of the desired prosthesis. Following shell production, the inner beads 20 are introduced into the shell through the hole so as to substantially fill the interior volume of the shell. After the beads are introduced into the shell, a patch (not shown) is affixed to the hole in the shell. The patch may have a self-sealing injection port (as described in U.S. Pat. Nos. 4,671,255; 5,084,061; 4,840,615) integral therewith to facilitate the addition of a fluid such as saline into the interior of the shell after the shell has been packed with the heads. To prevent sloshing and other problems it is important that during the addition of the fluid, all the air is removed from the interior volume of the shell. In this regard it is desirable to provide means for air to escape, preferably by inserting an air escape tube into the shell, either as a separate valve or through the self-sealing injection port, to provide fluid communication with the interior of the outer shell. This enables the air to escape or be forcibly evacuated as saline or some other fluid is injected.

As stated earlier, a variety of inner shells were made having a substantially spherical inner volume ranging in diameter from approximately 7/32 inch to 1/2 inch. In most cases, the holes perforating the wall of the inner shells were 1/16 inch in diameter, but they were as large as 3/32 inch in diameter. The wall thickness generally was in the vicinity of 0.010 inches to 0.013 inches. In general, the palpability of the individual inner shells within a saline-filled breast implant made in accordance with present specification, was not significantly different for the 1/2 inch inner shells when compared to the 7/32 inch diameter inner shells. The biggest difference between the large diameter inner shells and the small diameter inner shells was that the small diameter inner shells were more difficult to evacuate air from during the saline filling procedure.

We have described an adjunctive filler comprising hollow silicone beads having a plurality of fenestrations in the wall thereof which may be used to improve the properties of a fluid filled implant. While particular embodiments of the present invention have been illustrated and described, it would be obvious to those skilled in the art that various other changes and modifications can be made without departing from the spirit and scope of the invention. In particular, the adjunctive filler of the present invention may be used with any fluid filled prosthesis. The adjunctive filler of the present invention comprises a plurality of biocompatible hollow elastomeric shells having two or more holes perforating the wall thereof. The incorporation of the adjunctive filler into a fluid-filled prosthesis improves the hydraulic properties of the prosthesis filler material and helps retain the anatomical profile or elevation of the prosthesis. It is therefore intended to cover in the appended claims all such changes and modifications that are within the scope of this invention.

What we claim is:

1. A fluid-filled prosthesis comprising in combination, a) a shell comprising a flexible elastomer container having a first volume; (b) a fluid substantially filling said first volume; and (c) an adjunctive filler comprising at least one hollow bead, said bead having a substantially spherical elastomeric wall, an exterior surface and a spherical interior volume defining a cavity, said cavity being filled solely with said fluid and a plurality of holes penetrating said wall operable for providing fluid communication between said interior volume and said exterior surface of said bead.

2. The fluid-filled prosthesis of claim 1 comprising a plurality of said beads.

3. The fluid filled prosthesis of claim 1, wherein said prosthesis is implantable beneath the skin of a person.

4. The fluid filled prosthesis of claim 2, wherein said prosthesis is implantable beneath the skin of a person.

5. The fluid-filled prosthesis of claim 1, wherein said elastomic wall comprises silicone.

6. The fluid-filled prosthesis of claim 5, wherein said prosthesis is a breast prosthesis.

7. An adjunctive filler for a fluid-filled prosthesis, comprising a hollow, substantially spherical bead having a elastomeric wall, said wall enclosing a substantially spherical inner cavity, said cavity having an inner diameter and being filled solely with a homogeneous fluid and, wherein said bead has a substantially spherical outer surface, and at least two holes in said wall providing fluid communication between said outer surface and said inner cavity.

8. The adjunctive filler of claim 7, wherein said inner diameter of said bead is between 7/32 inch and 1/2 inch.

9. The adjunctive filler of claim 8, wherein said two holes have a diameter between 3/32 inch and 1/8 inch.

10. The adjunctive filler of claim 7, wherein said two holes have a diameter between 3/32 inch and 1/8 inch.

* * * * *